(12) United States Patent
Burgmeier et al.

(10) Patent No.: US 7,842,024 B2
(45) Date of Patent: Nov. 30, 2010

(54) MEDICAL DEVICE WITH VARYING PHYSICAL PROPERTIES AND METHOD FOR FORMING SAME

(75) Inventors: Robert E. Burgmeier, Plymouth, MN (US); Richard Goodin, Blaine, MN (US); Joseph Delaney, Jr., Minneapolis, MN (US); Larry Peterson, Champlin, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 12/562,760

(22) Filed: Sep. 18, 2009

(65) Prior Publication Data

US 2010/0010439 A1 Jan. 14, 2010

Related U.S. Application Data

(62) Division of application No. 10/749,821, filed on Dec. 31, 2003, now Pat. No. 7,601,285.

(51) Int. Cl.
*A61M 25/00* (2006.01)

(52) U.S. Cl. ...................................... 604/525

(58) Field of Classification Search ............... 604/525; 428/35.7; 264/211
See application file for complete search history.

(56) References Cited

U.S. PATENT DOCUMENTS

| | | | |
|---|---|---|---|
| 3,752,617 A | 8/1973 | Burlis et al. | |
| 4,110,283 A | 8/1978 | Capelle | |
| 4,276,250 A | 6/1981 | Satchell et al. | |
| 4,490,421 A | 12/1984 | Levy | |
| 4,663,471 A | 5/1987 | Shinohara et al. | |
| 4,722,344 A | 2/1988 | Cambron et al. | |
| 4,762,946 A | 8/1988 | Ritter et al. | |
| 4,906,244 A | 3/1990 | Pinchuk et al. | |
| 4,950,239 A | 8/1990 | Gahara et al. | |
| 5,088,991 A | 2/1992 | Weldon | |
| 5,096,848 A | 3/1992 | Kawamura | |
| 5,250,069 A | 10/1993 | Nobuyoshi et al. | |
| 5,258,160 A | 11/1993 | Utsumi et al. | |
| 5,264,260 A | 11/1993 | Saab | |
| 5,270,086 A | 12/1993 | Hamlin | |

(Continued)

FOREIGN PATENT DOCUMENTS

EP 0376656 7/1990

(Continued)

OTHER PUBLICATIONS

T.L. St. Clair and H.D. Burks, "Thermoplastic/Melt-Processable Polyimides," NASA Conf. Pub. *2334 (1984) pp. 337-355.

*Primary Examiner*—Nicholas D Lucchesi
*Assistant Examiner*—Brooke M Matney
(74) *Attorney, Agent, or Firm*—Vidas, Arrett & Steinkraus, P.A.

(57) ABSTRACT

A medical device in which a melt processed part has different crystallized properties at different locations. The part is formed of a polymer composition by inclusion a of polymer crystallization modifier in the composition making up at least a portion of such part, the amount of the polymer crystallization modifier is varied at different locations on the part in accordance with the desired difference in crystallization behavior.

9 Claims, 2 Drawing Sheets

U.S. PATENT DOCUMENTS

| | | | |
|---|---|---|---|
| 5,300,581 A | 4/1994 | Otawa et al. | |
| 5,306,246 A | 4/1994 | Sahatjian et al. | |
| 5,308,342 A | 5/1994 | Sepetka et al. | |
| 5,316,706 A | 5/1994 | Muni et al. | |
| 5,328,468 A | 7/1994 | Kaneko et al. | |
| 5,330,428 A | 7/1994 | Wang et al. | |
| 5,344,400 A | 9/1994 | Kaneko et al. | |
| 5,380,780 A | 1/1995 | Olson | |
| 5,500,180 A | 3/1996 | Anderson et al. | |
| 5,516,565 A | 5/1996 | Matsumoto | |
| 5,556,383 A | 9/1996 | Wang et al. | |
| 5,614,136 A | 3/1997 | Pepin et al. | |
| 5,797,877 A | 8/1998 | Hamilton et al. | |
| 5,980,532 A * | 11/1999 | Wang | 623/1.11 |
| 6,001,085 A | 12/1999 | Lurie et al. | |
| 6,030,405 A | 2/2000 | Zarbatany et al. | |
| 6,146,356 A | 11/2000 | Wang et al. | |
| 6,242,063 B1 | 6/2001 | Ferrera et al. | |
| 6,254,949 B1 | 7/2001 | Gluck et al. | |
| 6,270,522 B1 | 8/2001 | Simhambhatla et al. | |
| 6,284,333 B1 | 9/2001 | Wang et al. | |
| 6,319,454 B1 | 11/2001 | Nakagawa et al. | |
| 6,325,790 B1 | 12/2001 | Trotta | |
| 6,355,027 B1 | 3/2002 | Le et al. | |
| 6,358,227 B1 | 3/2002 | Ferrera et al. | |
| 6,358,450 B1 | 3/2002 | Sun | |
| 6,436,056 B1 | 8/2002 | Wang et al. | |
| 6,465,067 B1 | 10/2002 | Wang et al. | |
| 6,524,296 B1 | 2/2003 | Beals | |
| 6,524,299 B1 | 2/2003 | Tran et al. | |
| 6,552,123 B1 | 4/2003 | Katayama et al. | |
| 6,572,813 B1 | 6/2003 | Zhang et al. | |
| 6,585,688 B2 | 7/2003 | Ferrera et al. | |
| 6,596,296 B1 | 7/2003 | Nelson et al. | |
| 6,610,765 B1 | 8/2003 | Pfaendner et al. | |
| 6,765,059 B2 | 7/2004 | Corley | |
| 6,905,743 B1 | 6/2005 | Chen et al. | |
| 7,029,732 B2 | 4/2006 | Wang et al. | |
| 7,104,979 B2 | 9/2006 | Jansen et al. | |
| 7,128,956 B2 | 10/2006 | Wang et al. | |
| 7,387,826 B2 | 6/2008 | Burgmeier et al. | |
| 7,601,285 B2 | 10/2009 | Burgmeier et al. | |
| 2001/0027310 A1 | 10/2001 | Parisi et al. | |
| 2001/0041881 A1 * | 11/2001 | Sarge et al. | 604/525 |
| 2002/0045017 A1 | 4/2002 | Wang et al. | |
| 2003/0054161 A1 | 3/2003 | Forte et al. | |
| 2003/0148056 A1 | 8/2003 | Utz et al. | |
| 2003/0152728 A1 | 8/2003 | Wang et al. | |
| 2003/0167067 A1 | 9/2003 | Wang et al. | |
| 2004/0181271 A1 | 9/2004 | DeSimone et al. | |
| 2004/0241364 A1 | 12/2004 | Zihlmann | |
| 2005/0008806 A1 | 1/2005 | Schewe et al. | |
| 2005/0043679 A1 | 2/2005 | Devens, Jr. et al. | |
| 2005/0118370 A1 | 6/2005 | Varma et al. | |
| 2005/0233062 A1 | 10/2005 | Hossainy et al. | |

FOREIGN PATENT DOCUMENTS

| | | |
|---|---|---|
| EP | 1338300 | 8/2003 |
| JP | 2003062081 | 3/2003 |
| WO | 9421726 | 9/1994 |
| WO | 0001420 | 1/2000 |
| WO | 03051421 | 6/2003 |

* cited by examiner

US 7,842,024 B2

MEDICAL DEVICE WITH VARYING PHYSICAL PROPERTIES AND METHOD FOR FORMING SAME

CROSS REFERENCE TO RELATED APPLICATION

This is a division of U.S. application Ser. No. 10/749,821 filed Dec. 31, 2003, allowed.

BACKGROUND OF THE INVENTION

Various medical devices, such as catheters, tubes, balloons, stents and the like, are known to have physical performance requirements which change at particular points, or ranges of area or length. For instance, catheters typically need to be soft and flexible toward the distal end while at the same time becoming much more rigid and kink resistant proximally in order to effectively transmit torque and crossing forces from their proximal ends to the distal tip.

Medical devices comprising catheter balloons are used in an increasingly widening variety of applications including vascular dilatation, stent delivery, drug delivery, delivery and operation of sensors and surgical devices such as blades, and the like. The desired physical property profile for the balloons used in these devices vary according to the specific application, but for many applications a high strength robust balloon is necessary and good softness and trackability properties are highly desirable.

Commercial high strength catheter balloons have been formed of a wide variety of polymeric materials, including PET, nylons, polyurethanes, polyolefins, and various block copolymer thermoplastic elastomers.

U.S. Pat. No. 4,490,421, Levy, and U.S. Pat. No. 5,264,260, Saab, describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al and U.S. Pat. No. 6,146,356, Wang et al, describes balloons made from polyether-block-amide copolymers and polyester-block-ether copolymers. U.S. Pat. No. 6,270,522, Simhambhatla, et al, describes balloons made from polyester-block-ether copolymers of high flexural modulus. U.S. Pat. No. 5,344,400, Kaneko, describes balloons made from polyarylene sulfide. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, mention still further materials which may be used to make such balloons.

It has been found that polymers with a high content of butylene terephthalate can crystallize so extensively from an extrusion melt that balloon formation from an extruded parison is very difficult, if possible. A solution to this problem, taught in U.S. Pat. No. 6,465,067, Wang et al, is to add boric acid to the polymer composition.

In commonly owned copending U.S. application Ser. No. 10/055,747, medical devices formed of thermoplastic polymers containing chain extension additives which increase polymer molecular weight are described.

In commonly owned copending U.S. application Ser. No. 10/087,653, filed Feb. 28, 2002, incorporated herein by reference, it is disclosed that improved balloon properties can be obtained by controlling the parison extrusion in a manner which restricts the elongation of the parison material in the longitudinal direction. The application discloses that decreasing the gap between the extrusion head and the cooling bath tank can lower parison elongation by shortening the quench time.

In commonly owned copending U.S. application Ser. No. 10/617,428, filed Jul. 10, 2003, it is taught that varying the cooling tank gap during an extrusion can provide a catheter tube or balloon parison which has variable properties along its length.

In a balloon catheter, heat welded balloon-to-tube bonds, typically provided by laser heating, are commonly used for their high reliability. However, heat welded bonds provide a new problem, the melted or softened regions of the joined parts will often resolidify relatively slowly, allowing crystallization to develop with consequent increased rigidity. At the distal end of the catheter where the balloon is typically bonded to the catheter inner tube, the increased crystallinity in the bond can adversely affect the desired softness and trackability and of the catheter tip. Selecting a slow crystallizing polymer for the balloon material is usually not a suitable option since balloon material selection and processing steps are typically directed to maximizing balloon wall strength and hence providing a high degree of crystallization.

At the same time the catheter distal outer tube near the site, where it is bonded to the proximal waist of the balloon, often is subjected to very high tensile stress when the balloon is collapsed after use and is being withdrawn into a guide catheter or a protective sleeve. In some cases, particularly with larger balloons, the catheter shaft immediately proximal of the balloon may begin to yield before the balloon is successfully withdrawn. Consequently the tensile strength of the catheter outer can limit the minimum guide catheter or sleeve diameter which may be used with the catheter.

SUMMARY OF THE INVENTION

The present invention is directed to medical devices that are formed of thermoplastic material or materials, and to methods of forming such devices. In particular it is directed to such devices in which a melt processed part desirably has different crystallizing properties at different locations. In accordance with the invention the part is formed of a polymer composition by inclusion a of polymer crystallization modifier in the composition making up at least a portion of such part, the amount of the polymer crystallization modifier being varied in the part in accordance with the desired difference in crystallization behavior.

In one embodiment a catheter shaft is prepared by a technique in which the extruded tubing composition has a varying content of crystallization modifier along the tubing length. The catheter shaft may be an outer shaft in which the composition extruded to form the tubing distal end comprises a crystallization enhancer to locally increase the distal end tensile strength.

In another embodiment a tubular balloon parison is extruded with a composition which varies in composition by localized inclusion of a crystallization inhibitor. The portion of the parison which forms the distal waist of the balloon may be provided with such inhibitor in order to reduce the rigidity which develops upon heat welding of the balloon to the distal inner tube of the catheter.

Further aspects of the invention are described in the following detailed description of the invention or in the claims.

DETAILED DESCRIPTION OF THE INVENTION

Figure 1:
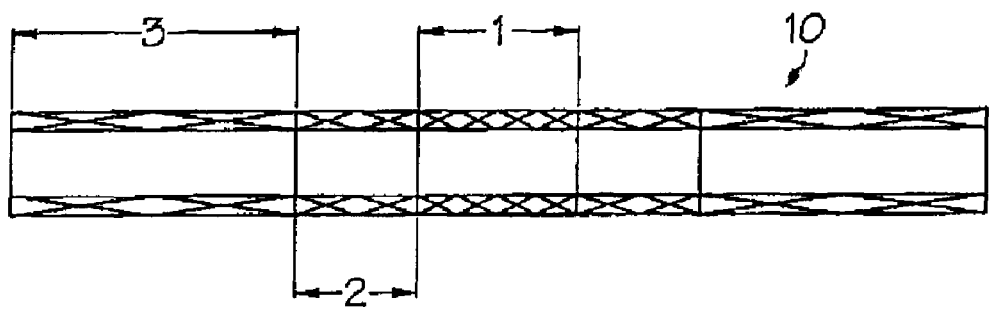
FIG. 1 is a schematic diagram of an extruded tubular balloon parison prepared in accordance with one embodiment of the present invention.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The medical device parts to which the invention may be applied include tubes, cannulae, catheter shafts, balloons and parisons therefor, stents, connectors, leads, or parts of any such devices. The part may be the entire device or a discretely formed portion thereof. It may be a layer of a laminate article.

The medical device part is formed of melt processed polymer material. The polymer material is formed of a polymer material composition which comprises a thermoplastic polymer or mixture thereof. In at least a portion of the part, the polymer composition further comprises a crystallization modifier. From a first portion of the inventive part to a second portion thereof, the composition is varied in the amount of crystallization modifier employed therein.

The invention may be used with any known semi-crystalline thermoplastic materials. Examples include olefin, acrylic and vinyl polymers and copolymers, polyethers polyamides, polyesters, polyurethanes, styrenic polymers, block copolymers and the like. More particularly such polymers included the polyesters PET, PEN, PPT, PBT and copolymers thereof; polyvinyl chloride; olefin polymers and copolymers including irradiated polyethylene, polypropylene, ultra-high molecular weight polyolefins, and olefin ionomers (copolymers of olefin monomers and a metal salt of an olefinic acid, such as (meth)acrylic acid, succinic acid, maleic acid or fumaric acid); polyamides including aliphatic and aromatic nylons; polyurethanes; and various thermoplastic elastomers. Illustrative aliphatic polyamides include nylon 6, nylon 64, nylon 66, nylon 610, nylon 610, nylon 612, nylon 46, nylon 9, nylon 10, nylon 11, nylon 12, and mixtures thereof. Illustrative aliphatic polyurethanes include TECOPHILIC resins available from Thermedices, Inc, and polyurethane block copolymers such as PELLETHANE 2363-75D. Illustrative optionally modified polyolefins include ENGAGE polymers and SURYLN ionomer modified polyolefins sold by DuPont Dow Elastomers, and EXACT polymers available from Exxon Chemical. High strength thermoplastic elastomers are preferred, especially polyamide/polyether block copolymers, including polyamide/polyether/polyesters such as sold under the PEBAX trademark, especially PEBAX 6333, 7033, and 7233, and polyester/polyether block copolymers such as sold under the HYTREL and ARNITEL trademarks, in particular ARNITEL EM 740 and HYTREL 8238. The parison may be extruded as a single layer or in multiple layers, for instance 3, 5, 7 or even more alternating layers of different polymers or polymer compositions. Blends of two or more such polymers may also be used.

Crystallization modifiers are known which enhance crystallization, for instance by providing more effective nucleation sites, increasing crystallization rate or by other mechanisms. Other crystallization modifiers inhibit crystallization, for instance by tying up nucleating sites or terminating crystal propagation, or by some other mechanism. Either way, the invention contemplates that the polymer modification can be introduced locally for instance in the course of extruding, injection molding, or the like.

Table 1 provides examples of various types of polymers and crystallization inhibitors which may be utilized therewith:

TABLE 1

| Polymer | Inhibitors |
|---|---|
| Poly(ethylene oxide) | Acrylamide polymers such as polyacrylamide and poly(N,N'-dimethyl acrylamide); Lithium (bis)trifluoromethanesulfonate imide; Ceramic powders (nanometer size); Perfluorinated polyphosphazine; Electrolyte salts (e.g. $LiAlO_2$; $LiClO_4$) |
| Polysaccharides | Lactose |
| Polyesters (e.g. PET); Poly(ester-ether) block copolymers; Poly(ester-ester) block copolymers | Thermotropic liquid crystalline polymers; Polycarbonates Boric acid |
| Styrene-acrylic copolymers (e.g. poly(styrene-co-N-dimethylaminoethyl methacrylate)) | Hydroquinone; Diaminophenylene |
| Polyolefins | Norbornene functionalized polymers Pour-point depressants for paraffinic hydrocarbon oils such as unsaturated ester polymers and/or copolymers described in U.S. Pat. No. 4,110,283; U.S. Pat. No. 4,663,471; and U.S. Pat. No. 4,762,946 Oligomer hydrocarbon resins |

Table 2 provides examples of various types of polymers and crystallization enhancers which may be utilized therewith:

TABLE 2

| Polymer | Enhancers |
|---|---|
| Polyolefins | Organic or mineral nucleating agents, such as 1,2,3,4-bis-(3,4-dimethylbenzylidene sorbitol), methyldibenzylidene sorbitol, calcium stearate, Irgaclear ® D, Irgaclear ® DM, Irgaclear ® B 215, Milad ® 3988 |
| Polyesters and polyester block copolymers | Diphenylketone $Eu(acac)_3 \cdot diPy$ $Mn(CH_3COO)_2 + SbO_3$ Selar ® resins (PET polyolefin blends) |
| Polyamides; Poly(amide-ether) block copolymers; Poly(amide-ether-ester) block copolymers | Polyamide/(acrylonitrile-butadiene-styrene terpolymer) Polyamide/(styrene-acrylonitrile copolymer) |

A polymer system employing a crystallization inhibitor is described in U.S. Pat. No. 5,306,246 (Sahatjian) in which PET/polyolefin blends (Selar® resins) are added to PET in amounts up to 20% by weight of the composition.

Another polymer system employing a crystallization inhibitor is described in WO 94/21726 in which single-layer oriented heat-shrinkable films are obtained from polymer compositions comprising an ethylene/α-olefin copolymer, a polymeric alloy (made up of a heterophasic composition in which an amorphous ethylene/propylene copolymer is dispersed in a homopolymeric propylene matrix) and/or a random copolymer of propylene with ethylene, and a crystallization inhibitor For this purpose the crystallization inhibitor may be one or more of aliphatic and aromatic hydrocarbon resins, aliphatic and aromatic copolymers, such as polymers and copolymers of piperylene, methylbutene, isobutene, vinyltoluene, indene, α-methylstyrene, polycyclodiene, etc.; hydrogenated $C_9$ resins; and pinene and rosin resins and terpene resins.

Nucleating agents which may be employed in the compositions as crystallization enhancers are known, for instance from US 20030054161, US 20030148056, and U.S. Pat. No. 6,610,765. As reported in these documents nucleating agents which have been used previously for polymer films include mineral nucleating agents and organic nucleating agents. Examples of mineral nucleating agents include carbon black, silica, kaolin, sodium bicarbonate and talc. Among the organic nucleating agents which have been suggested as useful in polyolefin films include salts of aliphatic mono-basic or di-basic acids or arylalkyl acids such as sodium succinate, sodium glutarate, sodium caproate, sodium 4-methylvalerate, sodium-2-2'-methylenebis(4,6-di-tert-butylphenyl)phosphate, aluminum phenyl acetate, and sodium cinnamate. Alkali metal and aluminum salts of aromatic and alicyclic carboxylic acids such as aluminum benzoate, sodium or potassium benzoate, sodium beta-naphtholate, lithium benzoate and aluminum tertiary-butyl benzoate also are useful organic nucleating agents. The free acids of the above mentioned salts may also be suitable. Benzenesulfonamides have been reported to be useful nucleating agents, as well as substituted sorbitol derivatives such as bis-(benzylidene) and bis-(alkylbenzilidine) sorbitols wherein the alkyl groups contain from about four to about eighteen carbon atoms. Particular such substituted sorbitol derivatives are compounds of formula I

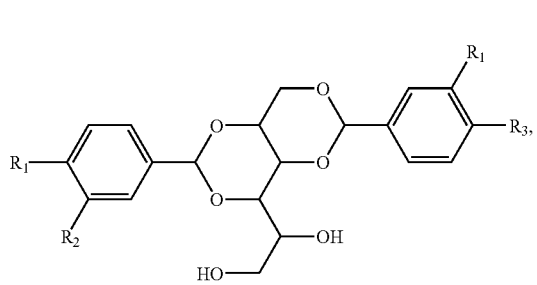

(I)

wherein $R_1$, $R_2$, $R_3$ and $R_4$ are each independently of one another hydrogen or $C_1$-$C_4$ alkyl, and $C_1$-$C_4$ alkyl is a branched or unbranched radical, for example methyl, ethyl, n-propyl, isopropyl, n-butyl, isobutyl or tert-butyl. Specific nucleating agents are the compounds of formula 1a (Irgaclear® DM), 1b (Irgaclear® D) and 1c (Millad® 3988).

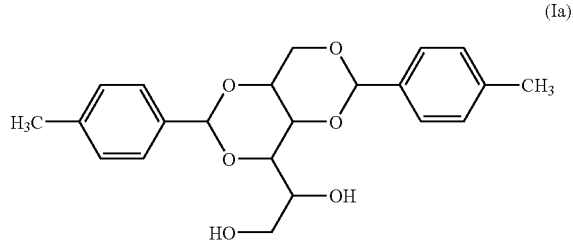

(Ia)

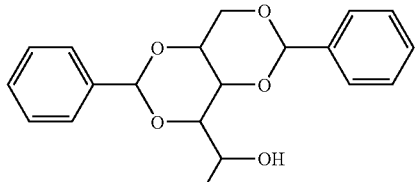

(Ib)

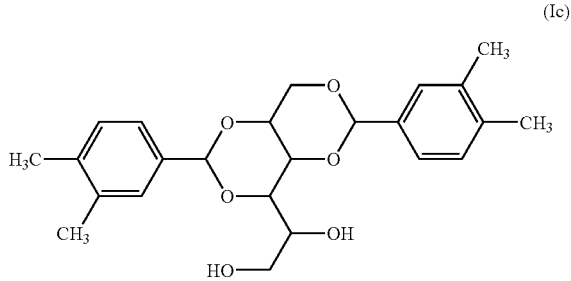

(Ic)

Irgaclear® DM and Irgaclear® D are registered trademarks of Ciba Spezialitatenchemie AG. Millad® 3988 is a registered trademark of Milliken & Company. Mixtures of any of the nucleating agents may be used, for instance a mixture of Irgaclear® DM and sodium benzoate. Other nucleating agents which can be used include phosphate ester based products such as NA-11 and NA-21 supplied by Asahi-Denka Kogyo of Japan, and a norbornane carboxylic acid salt based product HPN-68 supplied by Milliken & Company.

The nucleating agents described above are typically used with polyolefins, especially polypropylene polymers and copolymers, but in some polyethylene polymers or copolymers. Similar nucleating agents can be used for other semi-crystalline polymers.

The amounts of crystallization modifier incorporated into the formulations of the present invention will vary depending on their impact on the specific polymer employed in the composition and the degree of crystallization modification desired. In some cases quite small amounts, for instance as low as 100 ppm, may be suitable, especially in the case where the modifier is a nucleating agent, while in other cases amounts in excess of 3%, for instance up to 20% by weight may be suitable, particularity in the case of polymer or resinous crystallization inhibitors or up to 10% by weight in the case of nucleating agents. In accordance with the invention, varying the amount of the crystallization modifier by location within the inventive device part allows a more effective tailoring of properties of such part to localized differences in desired properties such as strength, softness, flexibility, distension and the like. The variation may be step-wise, or continuous, and it may range from zero to some positive amount, for example the modifier may be varied from zero to about 20% by weight of the polymer composition, from zero to about 10%, from 0.5% to about 5%, from 100 ppm to 2000 ppm, or from zero to about 3% by weight of the polymer composition.

A single medical device part may also be provided with more than one crystallization rate modifier. For instance a catheter inner shaft may be formed from a polymer composition comprising a crystallization rate enhancer in a proximal region, the enhancer tapering to zero moving distally. Then, at the distal end, a crystallization rate inhibitor may be incorporated into the composition. A polymer composition incorporating a crystallization enhancer may be used to form a catheter outer in the proximal region, the composition having a lesser or no amount of enhancer in an intermediate region and then once again incorporate an enhancer just proximal of the distal end to enhance resistance to necking during withdrawal of the catheter.

The composition variation employed in the invention can be coupled with concurrent complementary variations in extrusion or injection parameters which alter the available crystallization time, or device profile, to further increase the difference proximal to distal in stiffness, flexibility and/or other crystallization related physical properties. For instance a crystallization enhancer may be incorporated into an extrusion melt at the same time that the tank gap is changed to enhance longitudinal orientation and/or the tube diameter or wall thickness is increased. Crystalline structure in the formed part stabilizes polymer orientation obtained from processing operations such as extrusion, stretching, and parison blow-forming techniques, reducing creep relaxation which may occur over time or as a result of use stress.

Where the desired locality of the modified composition is small, extrusion and injection systems which allow changeover from one composition to another using very low volumes are preferably used. Where a gradual transition in properties is desired a wider range of composition supply systems can be used.

The invention has application to the preparation of preformed balloon parisons, for instance providing a crystallization inhibitor in the distal and/or proximal waist region to reduce crystallization during laser welding of the balloon to the catheter. Concurrently, or alternatively, in the portion of the parison used to form balloon body region a crystallization enhancer may be employed to reduce creep behavior and enhance the elastic response of the balloon after a first inflation.

In a multi-layer laminate catheter or balloon, crystallization modifiers may be employed in one or both layers. This may be desirable, for instance, to increase or decrease selected property differences between the two layers.

FIG. 1 shows an extruded balloon parison 10 prepared in accordance with an aspect of the invention, with crosshatching indicating the variation in composition. The segment has three distinct regions 1, 2, 3, each with different levels of crystallization. Region 3 has a crystallization inhibitor incorporated into the polymer composition and will produce a balloon waist portion which undergoes very little crystallization as a consequence of heat bonding to the catheter distal tip. Region 2 is a transition region as the composition changes over to an unmodified polymer composition in region 1. In subsequent processing operations region 1 will form the balloon body, region 2, will form the proximal cone, or a distal portion thereof, and region 3 will form a waist portion of the balloon.

Figure 2:
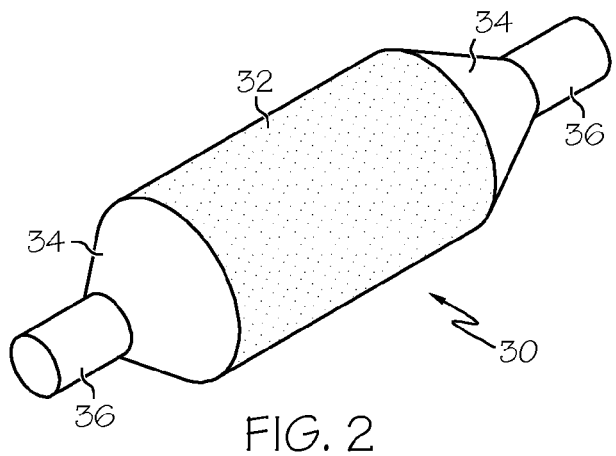
FIG. 2 is a perspective view of a balloon having body, waist and cone portions prepared in accordance with one embodiment of the present invention.

As discussed above, in the portion of the parison used to form balloon body region a crystallization enhancer may be employed to reduce creep behavior and enhance the elastic response of the balloon after a first inflation. FIG. 2 is a perspective view of a balloon 30 having body 32, waist 34 and cone 36 portions formed from this type of parison in which the crystallization enhancer is in the polymer composition used to form the body portion 32 of the balloon 30 (shown with stippling).

Figure 3:
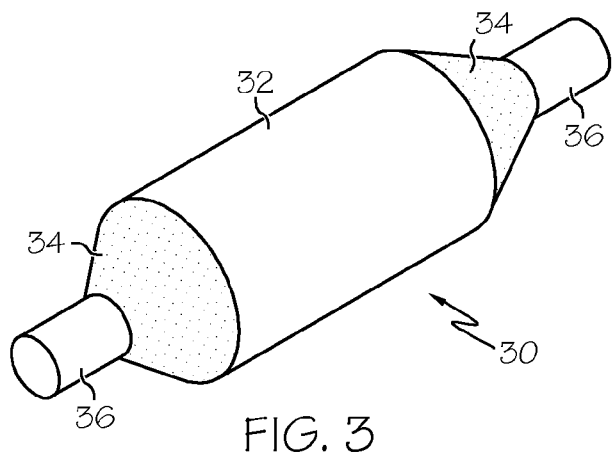
FIG. 3 is a perspective view of a balloon having body, waist and cone portions prepared in accordance with an alternative embodiment of the present invention.

In another embodiment illustrated by FIG. 3, balloon 30 having body 32, waist 34 and cone 36 portions is formed from a parison so that crystallization inhibitor is in the polymer composition so used to form the waist portions 34 of the balloon 30 (shown with stippling).

More complex patterns are also available. Stepped transitions may be produced, stepping progressively up or down, or both up and down in crystallization modifier, the length of transition region(s) may be different for different steps, or the variation in composition may be continuous. For instance using a single polymer, continuous variation of modifier component of the polymer composition over an elongated region of a catheter shaft may displace the need to manufacture the shaft in two or more segments of different polymers.

Differences in polymer modulus of as much as two times may be produced, relative to unmodified polymer, simply by the incorporation of an optimal amount of a crystallization inhibitor or enhancer. Even larger differences may be obtainable if the composition transitions from incorporation of an enhancer in one portion of the device to an inhibitor in another portion.

In a catheter shaft application, selective crystallization and tube wall reduction could enable a continuous tapered shaft from one material without the need for distal shaft bonds. This can be coupled with concurrent complementary variations in extrusion parameters which alter the available crystallization time, to further increase the difference proximal to distal in stiffness, flexibility and/or other crystallization related physical properties.

Figure 4:
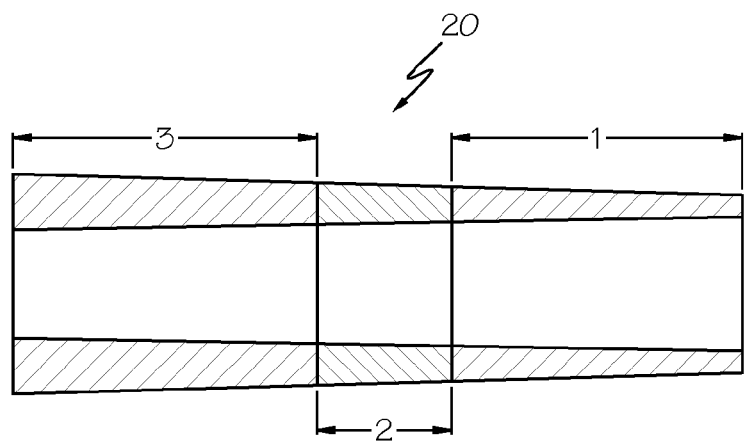
FIG. 4 is a longitudinal cross-section of a tapered catheter shaft in accordance with one embodiment of the present invention.

FIG. 4 shows an tapered catheter shaft 20 prepared in accordance with an aspect of the invention, with crosshatching indicating the variation in composition. The segment has three distinct regions 1, 2, 3, each with different levels of crystallization. Region 3 has a crystallization enhancer incorporated into the polymer composition and will produce catheter proximal region which undergoes a relatively higher level of crystallization as a consequence. Region 2 is a transition region as the composition changes over to region 1 wherein the polymer composition has crystallization inhibitor forming a region having a relatively lower level of crystallinity resulting in a more flexible distal region of the tapered catheter shaft.

In a multi-layer laminate catheter or balloon a crystallization modifier may be employed to increase property differences in the two layers.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A catheter tube or medical balloon having a length and comprising at least one layer of a polymer material composition that varies along its length,
   in at least a first portion of said length, the polymer material composition in said at least one layer comprises a thermoplastic base polymer and a crystallization enhancer, and
   in at least a second portion along said length the polymer material composition comprises said thermoplastic base polymer and a crystallization inhibitor.

2. A catheter tube of claim 1.

3. A catheter tube as in claim 2 wherein the variation of the polymer material composition of said at least one layer is continuous along said length.

4. A catheter tube as in claim 2 wherein the variation of the polymer material composition of said at least one layer is stepwise along said length.

5. A catheter tube as in claim 2 wherein said tube tapers continuously along said length, and said variation of the polymer composition is complementary to the taper so as to increase the difference proximal to distal in tube stiffness.

6. A medical balloon of claim 1.

7. A medical balloon as in claim 6 comprising waist, cone and body portions along said length, wherein said crystallization enhancer is located in at least a body portion.

8. A medical balloon as in claim 6 comprising waist, cone and body portions along said length, wherein said crystallization inhibitor is located in at least a waist portion.

9. A medical balloon as in claim 8 wherein said crystallization enhancer is located in at least a body portion.

* * * * *